United States Patent [19]

Komai et al.

[11] Patent Number: 4,970,244
[45] Date of Patent: Nov. 13, 1990

[54] PHOTOPOLYMERIZATION INITIATOR AND METHOD OF PHOTOPOLYMERIZATION BY USE OF SAID INITIATOR

[75] Inventors: Takeshi Komai, Aichi; Mamoru Shimizu, Tokoname, both of Japan

[73] Assignee: Nippon Oil & Fats Company, Ltd., Tokyo, Japan

[21] Appl. No.: 740,278

[22] Filed: Jun. 3, 1985

Related U.S. Application Data

[62] Division of Ser. No. 598,537, Apr. 10, 1984, abandoned.

[30] Foreign Application Priority Data

Apr. 26, 1983 [JP] Japan ................... 58-72277

[51] Int. Cl.$^5$ ............. C08F 2/50; C08F 4/36
[52] U.S. Cl. .......................... 522/46; 522/60
[58] Field of Search ........... 204/159.23; 260/453 RZ; 522/60, 46

[56] References Cited

U.S. PATENT DOCUMENTS

3,952,041 4/1976 D'Angelo et al.
4,171,252 7/1979 Fantazier.
4,338,171 7/1982 Barie, Jr. et al.
4,416,826 11/1983 Neckers ................ 260/453 RZ
4,604,295 8/1986 Humphreys et al. ......... 522/60

FOREIGN PATENT DOCUMENTS

126541 11/1984 European Pat. Off.
176777 4/1986 European Pat. Off.
23602 2/1982 Japan.
47727 3/1986 Japan.

OTHER PUBLICATIONS

Chimia y Technologia, vol. 6, 1980, pp. 23-25.
J. Org. Chem., vol. 44, No. 23, 1979, Thijs et al., "Photochemistry of Perester Initiators".
J. of the Am. Chemical Society, 93:25, Dec. 15, 1971, Leffler et al., "The Intra- and Intermolecular-Sensitized Photolysis of Substituted Benzoyl Peroxides", Chemical Abstracts, vol. 92, 1980, p. 188.
Chemical Reviews, vol. 68, No. 2, Mar. 25, 1968, Oster et al., "Photopolymerization of Vinyl Monomers".
J. Oil Col. Chem. Assoc. 1976, 59, 166-170, A. Pryce, "The Technological Literature Relating to Polymerization Photoinitiators".

Primary Examiner—Marion C. McCamish
Assistant Examiner—Arthur H. Koeckert
Attorney, Agent, or Firm—Oblon, Spivak, McClelland, Maier & Neustadt

[57] ABSTRACT

Photopolymerization initiators of the general formula:

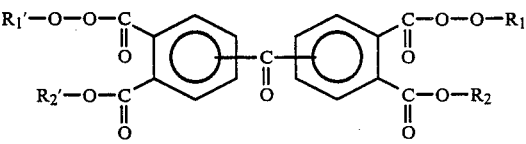

wherein $R_1$ and $R_1'$ independently stand for a tertiary alkyl group or a tertiary aralkyl group and $R_2$ and $R_2'$ independently stand for a hydrogen atom, a tertiary alkoxy group, or a tertiary aralkyloxy group are disclosed. They are useful for effecting polymerization of radically polymerizable unsaturated compounds.

4 Claims, 1 Drawing Sheet

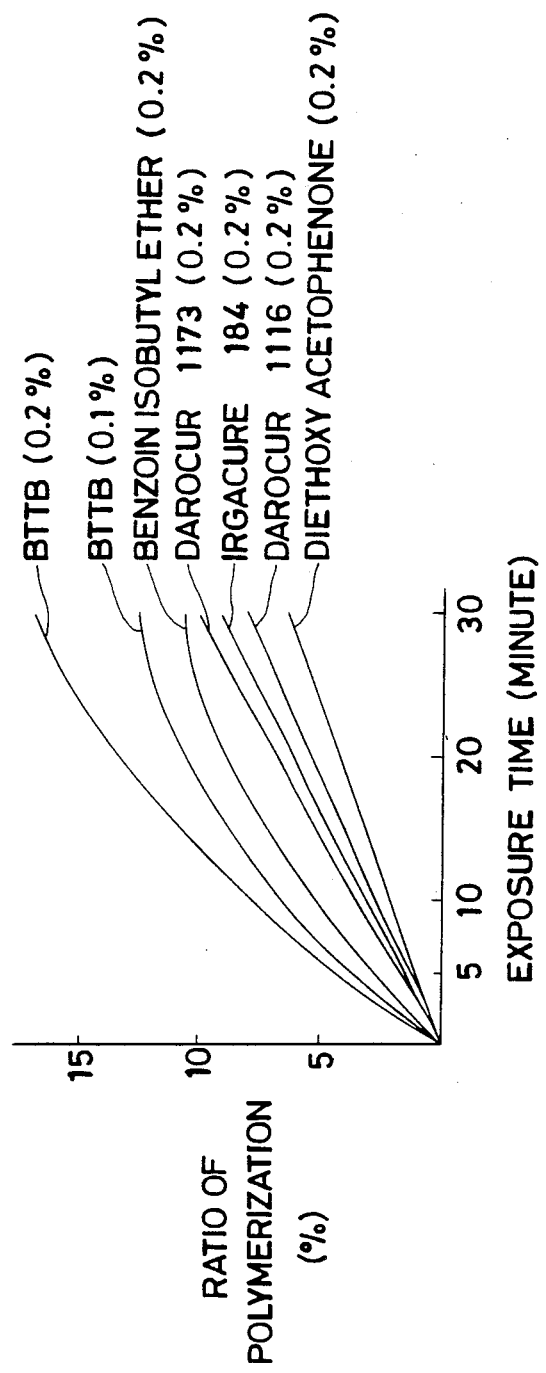

PHOTOPOLYMERIZATION INITIATOR AND METHOD OF PHOTOPOLYMERIZATION BY USE OF SAID INITIATOR

This is a division of application Ser. No. 598,537, filed Apr. 10, 10984, now abandoned.

BACKGROUND OF THE INVENTION:

This invention relates to a photopolymerization initiator having as its active component a specific benzophenone group-containing polyperoxyester and to a method for the polymerization of a radically polymerizable unsaturated compound by the use of the aforementioned photopolymerization initiator.

In polymerizing and setting photosensitive substances, the photopolymerization method and the photosetting method are advantageous over the thermopolymerizing method, the thermosetting method, and the oxidative setting method in respect that they permit polymerization and setting to be effected rapidly at low temperatures, offer high productivity, save energy, and avoid causing environmental pollution. Further, they are capable of providing selective setting. Owing to these numerous merits, these methods have found extensive utility in the production of printing inks, paints, adhesive agents, printing plates, and printed boards.

Various types of polymerization initiators have been developed for use in the photopolymerization method and the photo-setting method.

For example, such photopolymerization initiators as benzoin, benzoin ethers, benzyl, allyldiazonium salts, benzophenone derivatives, acetophenone derivatives, xanthates, thioxanthones, and halogenated hydrocarbons which generate radicals under the influence of ultraviolet rays have been known to the art (Journal of Oil and Color Chemists Association, Vol. 59, pp 166–170 (1976)).

It has also been known that such organic peroxides as benzoyl peroxide and di-t-butyl peroxide are usable as photopolymerization initiators. These organic peroxides generally absorb only the portion of light not exceeding 320 nm (Chemical Review, Vol. 68, pp 125–151 (1968)). Combined use of such organic peroxides with a sensitizer has been tried. For example, combinations of such organic peroxides as t-butyl peroxybenzoate and lauroyl peroxide with such photosensitizers as naphthalene, 1-naphthylaldehyde, and naphthylphenyl ketone have been proposed (U.S. Pat. No. 4,171,252). The elaborate incorporation of a sensitizer proves disadvantageous from the operational point of view. Moreover, such combinations entail the problem that the transfer efficiency of light energy from sensitizers to organic peroxides is low and the photocomposition efficiency of organic peroxides is low (Journal of American Chemical Society, Vol. 93, pp 7005–7012 (1971)). As a solution to this problem, adoption of organic peroxides of high photodecomposition property was tried. For example, U.S. Pat. No. 4,171,252 discloses use of 1-t-butylperoxycarbonyl naphthalene and Journal of Organic Chemistry, Vol. 44, pp 4123–4128 discloses use of 4-t-butylperoxycarbonyl benzophenone for photopolymerization of methyl methacrylate. These compounds, however, have been found to exhibit low polymerization activity.

Among the photopolymerization initiators so far accepted for practical use are counted Michler's ketone and thioxanthones. Michler's ketone has been reported as possessing a carcinogenic property (Chemical Abstract, Vol. 92, 123109Z) and thioxanthones have poor solubility (Japanese Patent Disclosure SHO 57(1982)23602).

As described above, the photopolymerization initiators developed to date have much room for further improvement.

An object of this invention is to provide a photopolymerization initiator that has no toxicity, possesses high thermal stability and high solubility, and is superior to any of the conventional photopolymerization initiators in terms of practical utility, and a method for polymerization by the use of the aforementioned polymerization initiator.

SUMMARY OF THE INVENTION

The object described above is accomplished by this invention using as a photopolymerization initiator a specific benzophenone group-containing polyperoxyester.

Specifically, the photopolymerization initiator of this invention is characterized by having as an active component thereof a benzophenone group-containing polyperoxyesters represented by the general formula (I):

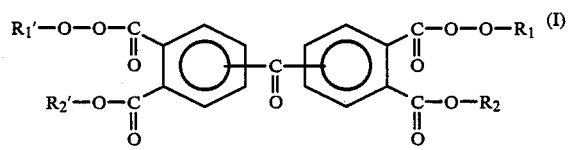

(wherein $R_1$ and $R_1'$ independently stand for a tertiary alkyl group of 4 to 8 carbon atoms or a tertiary aralkyl of 9 to 12 carbon atoms and $R_2$ and $R_2'$ independently stand for a hydrogen atom, a tertiary alkoxy group of 4 to 8 carbon atoms, or a tertiary aralkyloxy group of 9 to 12 carbon atoms).

This invention, therefore, relates to a photopolymerization initiator having as an active component thereof a benzophenone group-containing polyperoxyster represented by the general formula (I) and to a method for the polymerization of a photopolymerizable or photosetting unsaturated compound by the steps of mixing the compound with the photopolymerization initiator and exposing the resultant mixture to light.

BRIEF DESCRIPTION OF THE DRAWING

The drawing is a graph showing the relation between the duration of irradiation and the conversion with respect to photopolymerization initiators obtained in Examples 12, 13 and Comparative Experiments 8–12.

DESCRIPTION OF THE PREFERRED EMBODIMENTS

Numerous specific benzophenone group-containing polyperoxyesters are embraced by the general formula (I). Typical examples of such polyperoxyesters are as enumerated below.

First, the compounds represented by the following general formula (II) may be cited:

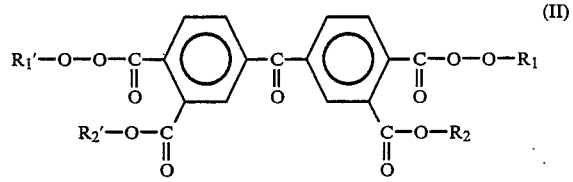

(II)

(wherein $R_1$ and $R_1'$ are the same as those of the general formula (I) and $R_2$ and $R_2'$ independently stand for a tertiary alkoxy group of 4 to 8 carbon atoms or a tertiary aralkyloxy group of 9 to 12 carbon atoms). The specific compounds embraced by the general formula (II) are also numerous; some have the same substituents for $R_1$ and $R_1'$ as those for $R_2$ and $R_2'$ and others have different substituents for $R_1$ and $R_1'$ from the substituents for $R_2$ and $R_2'$.

Now, typical compounds which have the same substituents for $R_1$ and $R_1'$ as those for $R_2$ and $R_2'$ will be cited.

3,3',4,4'-Tetra-(t-butylperoxycarbonyl)-benzophenone

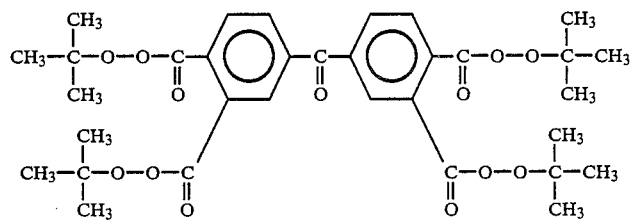

3,3',4,4'-Tetra-(t-amylperoxycarbonyl)-benzophenone

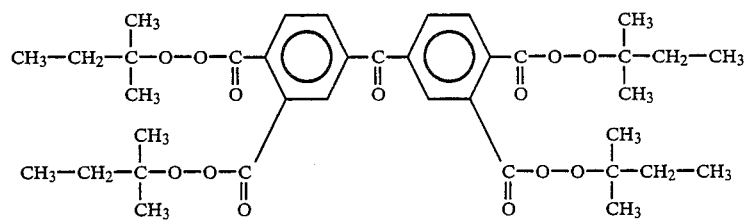

3,3',4,4'-Tetra-(t-hexylperoxycarbonyl)-benzophenone

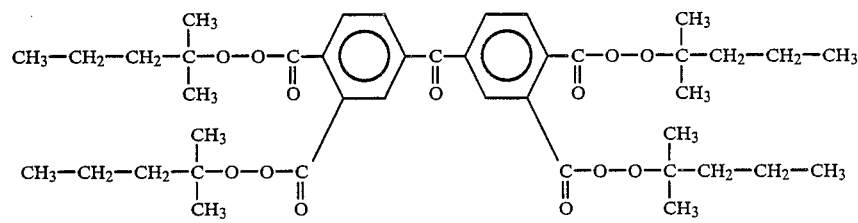

3,3',4,4'-Tetra-(t-octylperoxycarbonyl)-benzophenone

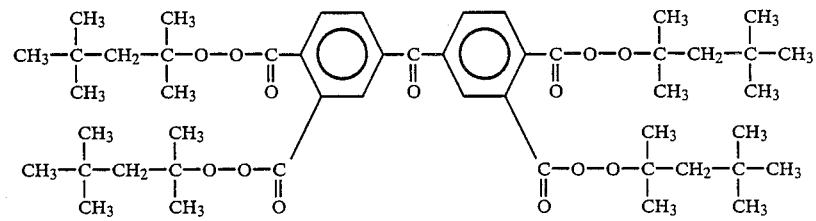

3,3',4,4'-Tetra-(t-cumylperoxycarbonyl)-benzophenone

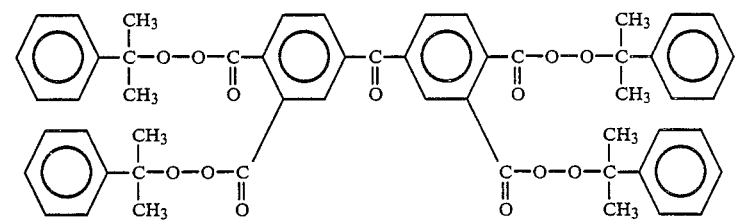

3,3',4,4'-Tetra-(p-isopropylcumylperoxycarbonyl)-benzophenone

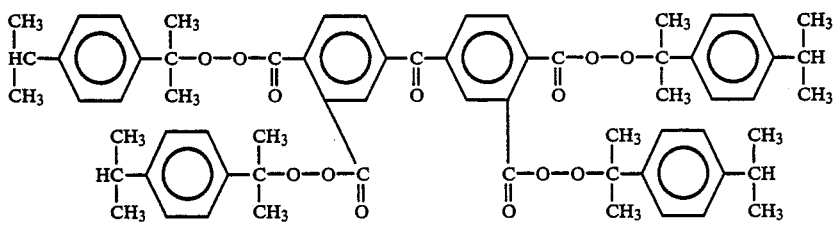

Then, the compounds which have hydrogen atoms substituted one each for $R_2$ and $R_2'$ in the general formula (I) are represented by the following general formula (III).

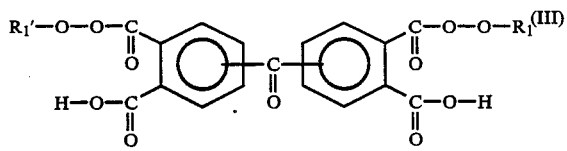

(wherein $R_1$ and $R_1'$ independently stand for a tertiary alkyl group of 4 to 8 carbon atoms and the carbonyl group has sites of substitution at the positions 4, 5).

Specific compounds of the general formula (III) are dicarboxy-di(t-butylperoxycarbonyl)-benzophenone and dicarboxy-di(t-hexylperoxycarbonyl)-benzophenone.

Dicarboxy-di(t-butylperoxycarbonyl)-benzophenone is a condensate of benzophenone-tetracarboxylic dianhydride with t-butylhydroperoxide. It is inferred to be a mixture of the compounds, 3,3'-dicarboxy-4,4'-di (t-butylperoxycarbonyl)-benzophenone, 3,',4 dicarboxy-3,4'-di(ti-butylperoxycarbonyl)-benzophenone and 4,4'-dicarboxy-3,3'-di(t-butylperoxycarbonyl)-benzophenone, which are represented respectively by the following formulas,

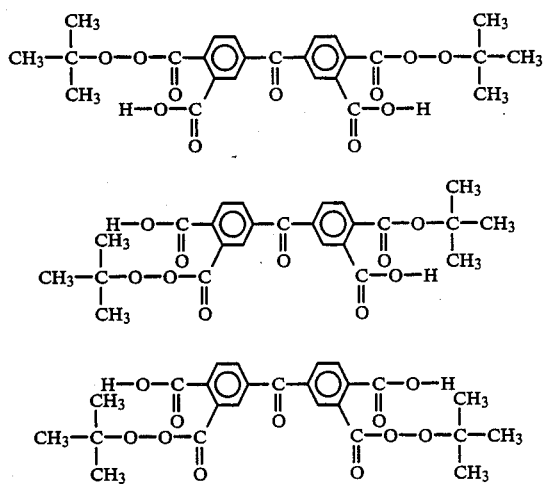

This theory applies to dicarboxy-di(t-hexylperoxycarbonyl)-benzophenone.

In the compounds cited above, 3,3',4,4'-tetra-(t-butylperoxycarbonyl)-benzophenone and dicarboxy-di(t-butylperoxycarbonyl)-benzophenone have been known to the art (Chimia y Technologia, Vol. 6, pp 23–25). Usability of these compounds as photopolymerization initiators, however, has been disclosed nowhere in literature.

The photopolymerization initiator of the present invention is composed of a benzophenone group serving as an ultraviolet ray absorbing group and two to four peroxyester groups bound to the aforementioned benzophenone group. As the numbers of carbon atoms in $R_1$, $R_1'$, $R_2$ and $R_2'$ are excessively large, the amount of radicals generated per unit weight is small and the activity is low. When $R_1$, $R_1'$, $R_2$, and $R_2'$ are primary or secondary substituents, the organic peroxide is deficient in stability. The carbonyl group does not bear on photopolymerization activity.

Now, the method by which the photopolymerization initiator of the present invention is produced will be described. The photopolymerization initiator is synthesized from benzophenone tetracarboxylic dianhydride and hydroperoxide as starting materials.

The compound represented by the general formula (II) is easily obtained by converting benzophenone tetracarboxylic dianhydride with a halogenating agent such as phosgene or thionyl chloride into an acid halide and causing this acid halide to react with hydroperoxide in the presence of an inorganic base such as sodium hydroxide or potassium hydroxide or an organic base such as pyridine or triethylamine.

The compound represented by the general formula (III) is obtained by the direct react-on of benzophenone tetracarboxylic dianhydride with hydroperoxide. For example, dicarboxy-di(t-butylperoxycarbonyl)-benzophenone is a condensate of benzophenone tetracarboxylic dianhydride with t-butyl hydroperoxide and is obtained in the form of the aforementioned mixture of three compounds. In the course of the reaction, a small amount of acetic acid, an acid compound such as p-toluenesulfonic acid, or a basic compound such as sodium hydroxide, potassium hydroxide, or pyridine may be used as a catalyst.

Now, the method of the present invention for photopolymerization will be described.

Desired photopolymerization or photosetting of a given radically polymerizable unsaturated compound is accomplished by the steps of mixing the compound with the photopolymerization initiator of this invention and exposing the resultant mixture to light. The mixture of at least one radically polymerizable unsaturated compound with the photopolymerization initiator of the present invention may suitably incorporate therein additives of popular use such as pigment, filler, dye, sensitizer, thermopolymerization inhibitor, plasticizer, and solvent. The photosensitive composition consequently produced is usable in the preparation of paints, adhesive agents, printing inks, printing plates, and printed wiring boards.

As radically polymerizable unsaturated compounds which can be photopolymerized or photoset in the presence of the photopolymerization initiator, polymerizable monomers, polymerizable oligomers, and polymerizable unsaturated monomers may be cited. The polymerizable monomers are compounds possessing at least one double bond. Examples of such polymerizable monomers include unsaturated carboxylic acids such as acrylic acid, methacrylic acid, maleic acid, fumaric acid, crotonic acid, and itaconic acid and derivatives of such unsaturated carboxylic acids such as monoesters including methyl (meth)acrylate, ethyl (meth)acrylate, butyl (meth)acrylate, 2-ethylhexyl (meth)acrylate, phenyl (meth)acrylate, and benzyl (meth)acrylate, hydroxyalkylesters including 2-hydroxyethyl (meth)acrylate and 2-hydroxypropyl (meth)acrylate, polyesters including ethylene glycol diacrylate, polyethylene glycol di(meth)acrylate, neopentyl glycol di-(meth)acrylate, trimethylolpropane tri-(meth)acrylate, and pentaerythritol tetraacrylate, (meth)acrylonitrile, (meth)acrylamide, and N-substituted (meth)acrylamide, v-nyl esters including vinyl acetate, vinyl propionate, vinyl acrylate, and vinyl succinate, vinyl ethers, and vinyl compounds including styrene, alkylstyrenes, halogenated styrenes, divinyl benzene, vinyl naphthalene, N-vinyl pyrrolidone, diallyl phthalate, diallyl malate, triallyl isocyanate, and triallyl phosphate.

Examples of polymerizable oligomers and polymerizable unsaturated polymers are curable resins possessing malate group, fumarate group, allyl group, and (meth)acrylate group, unsaturated polyesters, unsaturated acrylic resins, isocyanate-modified acrylate oligomers, epoxy-modified acrylic oligomers, polyester acrylic oligomers, and polyether acrylic oligomers.

Basically, the amount of the photopolymerization initiator of the present invention to be used is in the range of 0.01 to 10% by weight, preferably 0.1 to 4% by weight, as benzophenone group-containing polyperoxyester based on the radically polymerizable unsaturated compound. This amount, however, is affected by the kinds of additives incorporated and their amounts. When there is incorporated a pigment of inferior permeability to light, the amount may be increased. If the amount is too large, however, there may ensue a possibility that the resultant polymer will contain unaltered photopolymerization initiator and the physical properties of the polymer will be impaired. If this amount is too small, the polymerization does not proceed to the point of completion and the unsaturated compound partly remains unaltered.

Since the photopolymerization initiator of this invention has a benzophenone group as a light-absorbing group, it generates a radical and initiates the polymerization and setting reaction on absorption of the portion of light not exceeding 420 nm. Thus, the light source to be used during the course of photopolymerization and photosetting is satisfactory so far as it contains light having a shorter wavelength than 420 nm. Examples of light sources satisfying this requirement include sunlight mercury vapor lamp, hydrogen-discharge lamp, xenon arc lamp, flash-discharge lamp, tungsten lamp, halogen lamp, dye laser, and krypton ion laser.

Now, the characteristics of the photopolymerization initiator of this invention and the method for polymerization by the use of this photopolymerization initiator will be enumerated below.

(1) The photopolymerization initiator itself enjoys high thermal stability and permits easy handling because it has as a radical generating source a peroxyester group which has high thermal stability and does not readily yield to induced decomposition.

(2) For the reason as given in (1) above, the photopolymerizable composition containing the photopolymerization initiator can be preserved intact for a long time without undergoing polymerization and gelation.

(3) Since the polymerization initiator possesses the peroxyester group, it can be uniformly mixed easily at a desired proportion with the polymerizable unsaturated compound. Consequently, the polymerization reaction is allowed to proceed uniformly.

(4) Since the polymerization initiator contains a plurality of peroxyester groups in the molecular unit thereof, the amount of radicals generated per unit weight is large and the amount of the photopolymerization initiator required to be used can be proportionally decreased.

(5) Since the polymerization initiator is polyfunctional, the photopolymerization initiator itself serves as the point of crosslinking and accelerates the velocity of photosetting.

None of the known monofunctional photopolymerization initiators can constitute a crosslinking point.

(6) When the photopolymerization is carried out by the method of the present invention, the produced polymer has a high molecular weight. The method, therefore, can be expected to produce a polymer excelling in various properties such as strength and resistance to solvent.

(7) Since the polymerization initiator is polyfunctional, any photopolymerization initiator partially decomposed when the peroxyester group has low photodecomposition ratio is allowed to bind itself as initiator segments within the produced polymer. Thus, the possibility of the polymer exuding unaltered photopolymerization initiator is remote.

(8) The photopolymerization initiator of the present invention, on decomposition, by-produces benzophenone or benzophenone (poly)carboxylic acid, alcohols and ketones. These by-products, on analysis, are shown not to possess toxicity of the kind exhibited by Michler's ketone and poses no special problem from the standpoint of safety and hygiene.

Now, the method for the production of the photopolymerization initiator of the present invention and the physical properties of the product will be described specifically below with reference to referent examples

REFERENT EXAMPLE 1

3,3',4,4,'-Tetra-(t-butylperoxycarbonyl)-benzophenone (1) Synthesis

First, 3,3,'4,4,'-tetrachloroformyl benzophenone was synthesized. In a round bottom flask having an inner volume of 500 ml and fitted with a reflux condenser, 64.4 g of benzophenone tetracarboxylic dianhydride, 100 ml of benzene, 7 ml of dimethyl formamide, and 105 g of thionyl chloride were refluxed for 8 hours. The reaction mixture was then distilled under a vacuum to expel benzene and thionyl chloride and obtain lightly yellow slurry of 93.3 g of 3,3,'4,4,'-tetrachloroformyl benzophenone (chlorine content 28.5%, purity 86.8%, and yield 93.8%). By recrystallizing this slurry from chloroform, there was obtained a yellowish white solid (chlorine content 31.5%, purity 96%, melting point 113°–115° C., academically accepted m.p. 104° C.).

Then 19.85 g (0.15 mol) of 68% t-butyl hydroperoxide, 6.45 g (0.15 mol) of 93% sodium hydroxide, and 50 ml of water were charged into a four-necked round bottom flask having an inner volume of 100 ml, fitted with a stirrer and after that 54 g (0.025 mol) of a 20% benzene solution of the 3,3,'4,4,'-tetrachloroformyl benzophenone synthesized as described above was added dropwise into the said four-necked round bottom flask with stirring at a temperature lower than 10° C. After the addition, the resultant mixture was left to undergo reaction at 20° to 25° C. for 2 hours. The reaction mixture was then separated. The organic layer was washed twice with a dilute aqueous solution of sodium hydroxide and then washed with a saturated aqueous sodium chloride solution until neutrality. It was dried with anhydrous $MgSO_4$ and filtered. When the filtrate was concentrated, there was obtained a light yellow oily substance. By recrystallizing this oily substance from 20 ml of diethyl ether and 15 ml of n-hexane, there were obtained 12.8 g of light yellow crystals. By analyzing the light yellow crystals by various methods, there were obtained the results shown in Table 1. Thus, they were, identified to be 3,3',4,4'-tetra-(t-butylperoxycarbonyl)-benzophenone.

TABLE 1

| Elementary analysis (%) | C; 61.23 (Calculated - 61.29) H; 6.77 (Calculated - 6.55) |
|---|---|
| Infrared absorption spectrum $(cm^{-1})$ | 853 (—OO—linkage) 1765 ($-\overset{\overset{\displaystyle O}{\|}}{C}-O-$ linkage) 1678 ($-\overset{\overset{\displaystyle O}{\|}}{C}-$ linkage) |
| Nuclear magnetic resonance spectrum ($CDCl_3$, ppm) | 1.42 ⎫ (36H) (protone of t-butyl 1.44 ⎭ group) 7.93~8.25 (6H) (aromatic protone) |
| Ultraviolet absorption spectrum (in dioxane) | 255 nm ($\epsilon$ 24000) 347 nm ($\epsilon$ 175) |

(2) Physical properties

Various polymerization initiators of the present invention were prepared by following the procedure described above, analyzed for identification, and tested for physical constants. The results were as shown in Table 2.

omers, indicating that they have ample solubility for practical use.

(3) Velocity of thermal decomposition

The aforementioned 3,3,'4,4,'-tetra-(t-butylperoxycarbonyl)-benzophenone, a photopolymerization initiator of this invention, was tested for velocity of thermal decomposition in an initial concentration of 0.0125 mol/liter in cumene. Under the identical conditions, known peroxyesters were tested for the velocity of thermal decomposition. The results were as shown in Table 3.

TABLE 3

| | Name of compound | Constant velocity of thermal decomposition ($\times 10^{-5} sec^{-1}$) | |
|---|---|---|---|
| | | At 100° C. | At 120° C. |
| Photopolymerization initiator of this invention | 3,3',4,4'-Tetra-(t-butylperoxycarbonyl)-benzophenone | 1.0 | 14.3 |
| Known peroxyesters | t-Butylperoxybenzoate[1] | 3.5 | 35 |
| | 1-(t-Butylperoxycarbonyl)-naphthalene | 8.69 | — |
| | 4-(t-Butylperoxycarbonyl)-benzophenone | 2.88 | — |

[1]In a state dissolved in an unsaturated polyester, t-butylperoxybenzoate showed a pot life exceeding 3 months at room temperature.

Table 3 indicates that 3,3,'4,4,'-tetra-(t-butylperoxycarbonyl)-benzophenone, a photopolymerization initiator of this invention, possesses better thermal stability than known peroxyesters.

REFERENT EXAMPLE 2

Synthesis of dicarboxy-di(t-butylperoxycarbonyl)-benzophenone and physical properties thereof 16.1 g (0.05 mol) of benzophenone tetracarboxylic dianhydride, 10 ml of dioxane, and 14.4 g (0.15 mol) of 95% anhydrous t-butyl hydroperoxide were charged into a four-necked round bottom flask having an inner volume of 100 ml, fitted with a stirrer. Then the flask

TABLE 2

| Photopolymerization initiator of the present invention | Purity by iodometry (%) | Attribute | Melting point (°C.) | Refractive index (25° C.) | Solubility (25° C.) | |
|---|---|---|---|---|---|---|
| | | | | | Styrene | Methyl methacrylate |
| 3,3',4,4'-Tetra-(t-butylperoxycarbonyl)-benzophenone | 95.3 | Light yellow crystals | 110~111 | — | 97 | 90 |
| 3,3',4,4'-Tetra-(t-amylperoxycarbonyl)-benzophenone | 94.8 | Light yellow liquid | — | 1.5182 | Not less than 100 | Not less than 100 |
| 3,3',4,4'-Tetra-(t-hexylcarbonyl)-benzophenone | 98.1 | Light yellow liquid | — | 1.5099 | Not less than 100 | Not less than 100 |
| 3,3',4,4'-Tetra-(t-octylcarbonyl)-benzophenone | 92.5 | Light yellow liquid | — | 1.5023 | Not less than 100 | Not less than 100 |
| 3,3',4,4'-Tetra-(cumylperoxycarbonyl)-benzophenone | 93.1 | Light yellow liquid | — | 1.5346 | Not less than 100 | Not less than 100 |

Solubility: Amount, expressed in grams, of a given initiator dissolved in 100 g of a given monomer.

From Table 2, it is noted that the polymerization initiators of the present invention showed degrees of solubility exceeding 90 in the given polymerizable monwas maintained in a water bath and 10 ml of pyridine was added dropwise into the said flask over a period of 5 minutes. After the addition, the resultant mixture was left to undergo reaction at 25° C. for 3.5 hours. Then, the reaction mixture was neutralized to pH 3–4 by the addition of dilute hydrochloric acid. The organic phase consequently was extracted and separated from the reaction mixture with 100 ml of diethyl ether, washed with water, and dried with anhydrous MgSO$_4$. On addition of 50 ml of n-hexane, a light yellow liquid was formed in the organic phase. The organic phase having the light yellow liquid was immersed twice in 50 ml of n-hexane to expel unaltered t-butylhydroperoxide. It was concentrated under a vacuum. Consequently, there was obtained 19.2 g of a light yellow solid.

This light yellow solid, on analysis by various methods, was identified to be dicarboxy-di-(t-butylperoxycarbonyl)-benzophenone. It was then tested for physical constants. The results were as shown in Table 4.

TABLE 4

| | |
|---|---|
| Purity by iodometry (%) | 89 |
| Acid number   Found | 214 |
|   Theoretical | 223 |
| Melting point (°C.) | 150~160 |
| Ultraviolet absorption spectrum (in dioxane) | 255 nm (ε 22000) |
| | 340 nm (ε 200) |
| Infrared absorption spectrum (cm$^{-1}$) | 840 (—OO—linkage) |
| | 1765 (—C(=O)—O— linkage) |
| | 1655 (—C(=O)— linkage) |
| | 1730, 1700, 920 (—C(=O)—O—H group) |
| Nuclear magnetic resonance spectrum (CD$_3$C(=O)CD$_3$) (ppm) | 1.37–1.39 (18H) (methyl protone) |
| | 7.9~8.47 (6H) (aromatic protone) |
| Solubility in methyl methacrylate (at 25° C.) | 110 |

REFERENT EXAMPLE 3

Synthesis of dicarboxy-di(t-hexylperoxycarbonyl)-benzophenone and physical properties thereof From t-hexylhydroperoxide and benzophenone tetracarboxylic dianhydride as starting material, a yellow jellylike liquid (purity 90.8%) was obtained by following the procedure of Referent Example 2. When this liquid was analyzed by the same methods as used in Referent Example 2, it was identified to be dicarboxy-di(t-hexylperoxycarbonyl)-benzophenone. This compound was dissolved in methyl methacrylate in a desired proportion.

Now, polymerizations effected by the use of photopolymerization initiators of the present invention will be cited below as working examples in comparison with polymerizations carried out by using or not using known photopolymerization initiators, whereby it will be demonstrated that the photopolymerization initiators of this invention and the polymers produced by their use are excellent.

EXAMPLES 1–9

In a photopolymerization tube made of quartz, a photopolymerization initiator of this invention and methyl methacrylate containing no polymerization inhibitor were mixed, with the photopolymerization initiator in an amount varied as indicated in Table 5 based on 100 parts by weight of methyl methacrylate so that the initial concentration of the radical generating group would amount to 0.05 mol/liter (except for Examples 2, 3). The interior of the photopolymerization tube was displaced with nitrogen by the freezing and thawing method. Then, in a constant temperature bath at 30° C., the reaction mixture in the tube was irradiated for 10 minutes with the light from a 400-W high-pressure mercury vapor lamp (covered with a 100-mesh metal gauze to diminish the light to about one half) kept at a distance of 8 cm, with the aid of a merry-go-round type exposure device (Model MGR-P, made by Daika Industry). The resultant polymer was tested for conversion by the gravimetric method using precipitation of methanol. The spent methanol was concentrated and analyzed by iodometry to determine the amount of unaltered photopolymerization initiator exudated from the polymer. The polymer was preserved in a dark place at 30° C. for 24 hours and tested by the gravimetric method for conversion. The value of the conversion was reported as indicating the dark reactivity of the polymer. The results thus obtained are shown in Table 5.

COMPARATIVE EXPERIMENTS 1–4

By following the procedure of Examples 1–9, methyl methacrylate was polymerized by using known photopolymerization initiators in three experiments and using no photopolymerization initiator in one experiment. The resultant polymers were tested for conversion, amount of unaltered photopolymerization initiator exuded, and dark reactivity. The results were as shown in Table 5.

TABLE 5

| | Example | | | | | | | | | Comparative Experiment | | | |
|---|---|---|---|---|---|---|---|---|---|---|---|---|---|
| | 1 | 2 | 3 | 4 | 5 | 6 | 7 | 8 | 9 | 1 | 2 | 3 | 4 |
| Amount added (parts by weight/100 parts by weight of methyl methacrylate)$^1$ | | | | | | | | | | | | | |
| 3,3',4,4'-Tetra-(t-butyl-peroxycarbonyl)-benzophenone | 0.86 | 0.1 | 0.0086 | — | — | — | — | — | — | — | — | — | — |
| 3,3',4,4'-Tetra-(t-amyl-peroxycarbonyl)-benzophenone | — | — | — | 0.94 | — | — | — | — | — | — | — | — | — |
| 3,3',4,4'-Tetra-(t-hexyl-peroxycarbonyl)-benzophenone | — | — | — | — | 1.01 | — | — | — | — | — | — | — | — |
| 3,3',4,4'-Tetra-(t-octyl-peroxycarbonyl)-benzophenone | — | — | — | — | — | 1.16 | — | — | — | — | — | — | — |
| 3,3',4,4'-Tetra-(cumylperoxy-carbonyl)-benzophenone | — | — | — | — | — | — | 1.19 | — | — | — | — | — | — |
| Dicarboxy-di(t-butylperoxy-carbonyl)-benzophenone | — | — | — | — | — | — | — | 1.34 | — | — | — | — | — |
| Carbonyl-di-(t-hexylperoxy- | — | — | — | — | — | — | — | — | 1.49 | — | — | — | — |

TABLE 5-continued

| | Example | | | | | | | | | Comparative Experiment | | | |
|---|---|---|---|---|---|---|---|---|---|---|---|---|---|
| | 1 | 2 | 3 | 4 | 5 | 6 | 7 | 8 | 9 | 1 | 2 | 3 | 4 |
| dihydrogen-diphthalate) | | | | | | | | | | | | | |
| Benzoin isobutyl ether[2] | — | — | — | — | — | — | — | — | — | 1.43 | — | — | — |
| 1-(t-Butylperoxy-carbonyl)-naphthalene[3] | — | — | — | — | — | — | — | — | — | — | 1.30 | — | — |
| 4-(t-Butylperoxy-carbonyl)-benzophenone[4] | — | — | — | — | — | — | — | — | — | — | — | 1.59 | — |
| Photopolymerization | | | | | | | | | | | | | |
| Conversion of photopolymerization (%) | 15.6 | 8.9 | 2.7 | 15.8 | 15.7 | 14.3 | 14.6 | 11.0 | 10.5 | 7.2 | 6.1 | 5.8 | 0.3 |
| Amount of unaltered photopolymerization initiator exuded (%) | 25 | 3 | 1 max. | 27 | 24 | 26 | 23 | 52 | 50 | Not tested | 75 | 70 | — |
| Dark reactivity (%) | 1 | 0.6 | Not tested | 1.1 | 1 | 0.9 | 0.9 | 0.8 | 0.8 | 4.3 | 2.9 | 1.3 | 0 |

[1]Calculated as reduced to purity;
[2]Reagent Grade 1, produced by Tokyo Chemical;
[3]Product synthesized in laboratory (purity 98.2%);
[4]Product synthesized in laboratory (purity 96.8%).

Table 5 indicates that in the working examples of this invention in which the radical generating groups were present in a fixed initial concentration, except for Examples 2, 3, the conversions of photopolymerization were high, the amounts of unaltered photopolymerization initiators exuded from the corresponding polymers were small, and the degrees of dark reactivity were low. These results testify that the photopolymerization initiators of the present invention are excellent.

EXAMPLES 10-11

A photopolymerization tube made of quartz was charged with methyl methacrylate having dissolved therein a photopolymerization initiator of this invention indicated in Table 6 in an amount adjusted to give a fixed radical generating group concentration of 0.006 mol/liter. The interior of the tube was displaced with nitrogen by the freezing and thawing method. Then, the tube was immersed into a water bath at 20° C. and the mixture in the tube maintained at 20° C. was irradiated for 10 minutes with the light from a mercury vapor lamp covered with a glass filter, Model UVD36-A made by Toshiba, instead of the metal gauze used in Examples 1-9 so as to adjust the main wavelength of the emanating light to 366 nm, with the aid of the same exposure device as used in Examples 1-9. The resultant reaction mixture was treated by the methanol precipitation method to collect the produced polymethyl methacrylate. This polymer was tested by gel permeation chromatography (with apparatus, Model HLC 802 UR, made by Toyo Soda) to determine the molecular weight of the polymer as reduced to styrene. The results were as shown in Table 6.

COMPARATIVE EXPERIMENTS 5-7

The procedure of Examples 10-11 was repeated, except that known photopolymerization initiators were used in the place of the photopolymerization initiators of the present invention. The resultant polymers similarly tested for molecular weight as reduced to styrene.

TABLE 6

| | Photopolymerization initiator | Molecular weight | |
|---|---|---|---|
| | | Weight-average | Number-average |
| Example | | | |
| 10 | 3,3',4,4'-Tetra-(t-butylperoxy-carbonyl)-benzophenone | 62200 | 33600 |
| 11 | Dicarboxy-di(t-butylperoxy-carbonyl)-benzophenone | 37700 | 22000 |
| Comparative Experiment | | | |
| 5 | 1-(t-Butylperoxycarbonyl)-naphthalene | 34600 | 18300 |
| 6 | 4-(t-Butylperoxycarbonyl)-benzophenone | 29300 | 16000 |
| 7 | Benzoin isobutyl ether | 29800 | 18200 |

Comparison of the data for Examples 10-11 with those for Comparative Experiments 5, 6, and 7 reveals that the polymers of Examples 10-11 were greater than those of Comparative Experiments 5, 6, and 7, testifying that use of the photopolymerization initiators of the present invention gives polymers of larger molecular weights than the use of conventional photopolymerization initiators.

EXAMPLES 12-13

By following the procedure of Examples 10-11 and using the same apparatus as used in Examples 10-11, methyl methacrylate was polymerized by using 3,3,'4,4,'-tetra-(t-butylperoxycarbonyl)-benzophenone at a varying concentration of 0.1 to 0.2% by weight, with the length of exposure time varied. The resultant polymer was tested for conversion by the same method as used in Examples 1-9 and then tested for molecular weight by the procedure of Examples 10-11. The relation between the exposure time and the conversion is shown in the drawing. The conversion, the velocity of polymerization ($R_p$), and the molecular weight obtained of the polymer after 30 minutes' exposure were as shown in Table 7.

In the diagram, BTTB stands for 3,3,'4,4,'-tetra-(t-butylperoxycarbonyl)-benzophenone.

COMPARATIVE EXPERIMENTS 8-12

Methyl methacrylate was polymerized by following the procedure of Examples 12, 13, except that a photopolymerization initiator shown in Table 7 was used in 3,3,',4,4,'-tetra-(t-butylperoxycarbonyl)-benzophenone.

The relation between the exposure time and the conversion was as shown in the drawing. The conversion, the velocity of conversion, and the molecular weight obtained after 30 minutes' exposure were as shown in Table 7.

EXAMPLES 20-21

On a plate glass plate, an ultraviolet ray curing resin solution (a 4/6 mixture of Aronix M-8060 (produced by Toa Chemical) and Aronix M-5700 (produced by

TABLE 7

|  | Example | | Comparative Experiment | | | | |
|---|---|---|---|---|---|---|---|
|  | 12 | 13 | 8 | 9 | 10 | 11 | 12 |
| 3,3',4,4'-Tetra-(t-butylperoxycarbonyl)-benzophenone | 0.1 | 0.2 | | | | | |
| Benzoin isobutyl ether[1] | | | 0.2 | | | | |
| 2-Hydroxy-2-methyl-1-phenyl-propan-1-one[2] | | | | 0.2 | | | |
| 1-Hydroxy-cyclohexyl-phenyl ketone[3] | | | | | 0.2 | | |
| 1-(4-Isopropylphenyl)-2-hydroxy-2-methyl-propan-1-one[4] | | | | | | 0.2 | |
| Diethoxy acetophenone[5] | | | | | | | 0.2 |
| Conversion after 30 minutes' exposure to light (%) | 12.63 | 17.00 | 10.80 | 10.24 | 9.38 | 8.13 | 6.41 |
| Velocity of polymerization ($R_p \times 10^3$) (mol/l · sec) | 1.06 | 1.20 | 0.76 | 0.53 | 0.46 | 0.42 | 0.33 |
| Weight-average molecular weight | 72000 | 44200 | 26800 | 46000 | 30000 | 49000 | 52000 |
| Number-average molecular weight | 24000 | 19000 | 13000 | 22000 | 17000 | 22000 | 27000 |

[1]Reagent Grade 1, made by Tokyo Chemical
[2]"Darocur 1173"; made by Merck
[3]"Irgacure 184"; made by Ciba Geigy
[4]"Darocur 1116"; made by Merck
[5]Product of Upjohn Co.

It is noted from the drawing and Table 7 that 3,3,'4,4,'-tetra-(t-butylperoxycarbonyl)-benzophenone gave higher conversion in polymerization and enjoyed higher photopolymerization activity than known photopolymerization initiators. It is further noted that although the polymerization with 3,3,'4,4,'-tetra-(t-butyl-peroxycarbonyl)-benzophenone had higher velocity, the produced polymer showed no fall of molecular weight.

EXAMPLES 14-19

To demonstrate that the photopolymerization initiators of the present invention are effective on various radically unsaturated compounds, a monomer indicated in Table 8 was photopolymerized in the presence of 3,3,'4,4,'-tetra-(t-butylperoxycarbonyl)-benzophenone by using the same exposure device, lamp, and filter as used in Examples 10-11. The produced polymer was tested for conversion by the gravimetric method. The results were as shown in Table 8.

TABLE 8

| Example | 14 | 15 | 16 | 17 | 18 | 19 |
|---|---|---|---|---|---|---|
| Amount added (parts by weight) | | | | | | |
| Polymerizable monomer | | | | | | |
| Acrylic acid[1] | 100 | | | | | |
| Acrylonitrile[2] | | 100 | | | | |
| 2-Hydroxyethyl acrylate[3] | | | 100 | | | |
| Trimethylol-propane triacrylate[4] | | | | 100 | | |
| Vinyl acetate[2] | | | | | 100 | |
| Styrene[2] | | | | | | 100 |
| Benzene | 334 | | 324 | 324 | | |
| 3,3',4,4'-tetra-(t-butylperoxycarbonyl)-benzophenone | 0.81 | 1.08 | 0.78 | 0.78 | 0.93 | 0.89 |
| Exposure time (minutes) | 2 | 10 | 2 | 2 | 10 | 10 |
| Conversion (%) | 80 | 8.8 | 89.2 | 98.3 | 15.0 | 1.0 |

[1]Reagent Supergrade, made by Wako Pure Chemical Industry;
[2]Pure product containing no polymerization inhibitor;
[3]Reagent Grade 1, made by Tokyo Chemical Industry;
[4]Product by Tokyo Chemical Industry.

Toagosei Chemical Industry)) containing an amount of 3,3',4,4'-tetra-(t-butylperoxycarbonyl)-benzophenone indicated in Table 9 was spread in a layer thickness of 50 μm. In a conveyor type ultraviolet ray curing device (light focusing type), the glass plate carrying the applied layer thereon was irradiated with the ultraviolet ray at a conveyor speed of 5 m/min. to cure the resin. The cured resin was tested for curing velocity by the method indicated below. The source of the light used for the curing was one 2-KW (80 W/cm) ozoneless type high-pressure mercury vapor lamp which was kept at a distance of 10 cm from the glass plate in motion on the conveyor. The results of the test were as shown in Table 9. Method for testing the curing velocity.

The number of passes a given applied layer had to make for the layer to acquire the pencil hardness of 5H was reported as indicating the curing velocity. Thus, this number is in inverse proportion to the curing velocity.

COMPARATIVE EXPERIMENTS 13-16

The same ultraviolet ray curing resin was cured by following the procedure of Examples 20-21, except that a known photopolymerization initiator indicated in Table 9 was used in the place of 3,3',4,4,'-tetra-(t-butyl-peroxycarbonyl)-benzophenone. In the course of the curing, the resin was tested for curing velocity. The results were as shown in Table 9.

TABLE 9

|  | Example | | Comparative Experiment | | | |
|---|---|---|---|---|---|---|
|  | 20 | 21 | 13 | 14 | 15 | 16 |
| 3,3',4,4'-Tetra-(t-butylperoxycarbonyl)-benzophenone | 1.0 | 2.0 | | | | |
| 1-Hydroxycyclohexyl-phenyl ketone[1] | | | 2.0 | | | |
| 2-Hydroxy-2-methyl-1-phenyl-propane-1-one[2] | | | | 2.0 | | |
| Benzoin-isobutyl ether[3] | | | | | 2.0 | |
| Diethoxy acetophenone[4] | | | | | | 2.0 |

TABLE 9-continued

|  | Example | | Comparative Experiment | | | |
|---|---|---|---|---|---|---|
|  | 20 | 21 | 13 | 14 | 15 | 16 |
| Curing velocity (number of passes) | 4 | 3 | 4 | 5 | 7 | 7 |

[1]"Irgacure 184"; made by Ciba Geigy
[2]"Darocur 1173"; made by Merck
[3]Reagent Grade 1, made by Tokyo Chemical
[4]Product of Upjohn Co.

It is noted from the foregoing table that 3,3',4,4'-tetra-(t-butylperoxycarbonyl)-benzophenone showed higher curing velocity than any of the conventional photopolymerization initiators.

What is claimed is:

1. A method for the photopolymerization of a radically polymerizable unsaturated compound, comprising the steps of:

adding to said radically polymerizable unsaturated compound a photopolymerization initiator having as an active component thereof a benzophenone group-containing peroxyester represented by the general formula

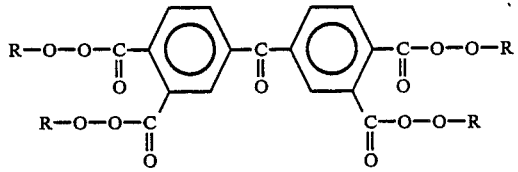

wherein each R is independently selected from the group consisting of $C_4$–$C_8$ tertiary alkyl groups and $C_9$–$C_{12}$ tertiary aralkyl groups, and exposing the resultant mixture to light.

2. The method according to claim 1, wherein all of said R groups are identical.

3. A method according to claim 1, wherein said radically polymerizable unsaturated compound capable of photopolymerization and photo-setting is at least one member selected from the group consisting of polymerizable monomers, polymerizable oligomers, and polymerizable unsaturated monomers.

4. A method according to claim 1, wherein the amount of said photopolymerization initiator to be added is in the range of 0.01 to 10% by weight as active component based on the amount of said radically polymerizable unsaturated compound.

* * * * *